United States Patent
Blacker

(10) Patent No.: US 10,953,206 B2
(45) Date of Patent: *Mar. 23, 2021

(54) ROBOTICALLY SHAPING A GUIDE WIRE TIP

(71) Applicant: Corindus, Inc., Waltham, MA (US)

(72) Inventor: Steven J. Blacker, Framingham, MA (US)

(73) Assignee: Corindus, Inc., Waltham, MA (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/142,215

(22) Filed: Sep. 26, 2018

(65) Prior Publication Data

US 2019/0167953 A1     Jun. 6, 2019

Related U.S. Application Data

(63) Continuation of application No. 14/216,728, filed on Mar. 17, 2014, now Pat. No. 10,085,805.

(60) Provisional application No. 61/790,792, filed on Mar. 15, 2013.

(51) Int. Cl.
| | |
|---|---|
| A61B 5/00 | (2006.01) |
| A61M 25/09 | (2006.01) |
| A61B 34/30 | (2016.01) |
| A61M 25/01 | (2006.01) |
| A61B 34/00 | (2016.01) |
| A61B 34/20 | (2016.01) |
| A61B 34/35 | (2016.01) |
| A61B 46/10 | (2016.01) |
| A61F 2/958 | (2013.01) |
| A61B 17/00 | (2006.01) |
| A61F 2/95 | (2013.01) |

(52) U.S. Cl.
CPC ....... *A61M 25/09041* (2013.01); *A61B 34/20* (2016.02); *A61B 34/30* (2016.02); *A61B 34/35* (2016.02); *A61B 34/73* (2016.02); *A61B 34/74* (2016.02); *A61B 46/10* (2016.02); *A61F 2/958* (2013.01); *A61M 25/0127* (2013.01); *A61B 2017/00477* (2013.01); *A61B 2034/2059* (2016.02); *A61B 2034/301* (2016.02); *A61F 2/9517* (2020.05); *A61M 2025/09108* (2013.01)

(58) Field of Classification Search
CPC ............ A61M 25/09; A61M 25/09041; A61M 2025/0183; A61M 2025/09125; A61B 5/6851; A61B 8/12
USPC .......................................... 600/585; 604/528
See application file for complete search history.

(56) References Cited

U.S. PATENT DOCUMENTS

| | | | | |
|---|---|---|---|---|
| 3,866,458 A | * | 2/1975 | Wagner | A61B 17/8863 72/459 |
| 4,368,023 A | * | 1/1983 | Hannah | A61M 25/001 249/111 |
| 4,716,757 A | * | 1/1988 | McGregor | A61M 25/09041 140/106 |
| 5,957,941 A | * | 9/1999 | Ream | A61B 8/4461 600/443 |
| 6,096,004 A | * | 8/2000 | Meglan | A61B 34/75 604/95.01 |
| 6,726,675 B1 | * | 4/2004 | Beyar | A61M 25/0105 600/106 |

(Continued)

*Primary Examiner* — May A Abouelela

(57) ABSTRACT

A robotic system for driving a guide wire into a human patient includes a robotic tool to change shape the tip of the guide wire and a robotic control system providing signals to operate the guide wire shaping tool.

19 Claims, 3 Drawing Sheets

(56) References Cited

U.S. PATENT DOCUMENTS

| | | | |
|---|---|---|---|
| 7,887,549 B2 | 2/2011 | Wenderow et al. | |
| 8,257,302 B2 * | 9/2012 | Beyar | A61B 34/77 |
| | | | 600/106 |
| 8,600,477 B2 * | 12/2013 | Beyar | A61B 6/12 |
| | | | 128/899 |
| 8,694,157 B2 * | 4/2014 | Wenderow | A61B 34/20 |
| | | | 700/245 |
| 8,790,297 B2 * | 7/2014 | Bromander | A61B 34/30 |
| | | | 604/95.01 |
| 9,901,705 B2 | 2/2018 | Armour et al. | |
| 2005/0277851 A1 * | 12/2005 | Whittaker | A61M 25/0158 |
| | | | 600/585 |
| 2006/0253048 A1 * | 11/2006 | Jones | A61M 25/09041 |
| | | | 600/585 |
| 2007/0106247 A1 * | 5/2007 | Burnett | A61M 1/28 |
| | | | 604/508 |
| 2007/0118079 A1 * | 5/2007 | Moberg | A61F 2/95 |
| | | | 604/164.07 |
| 2007/0276216 A1 * | 11/2007 | Beyar | A61B 5/062 |
| | | | 600/407 |
| 2008/0097298 A1 * | 4/2008 | Fisher | A61M 25/0147 |
| | | | 604/103.04 |
| 2009/0247944 A1 * | 10/2009 | Kirschenman | A61B 34/37 |
| | | | 604/95.04 |
| 2010/0130987 A1 * | 5/2010 | Wenderow | A61M 25/0113 |
| | | | 606/130 |
| 2010/0147048 A1 * | 6/2010 | Christofilis | B21F 1/00 |
| | | | 72/372 |
| 2010/0269950 A1 * | 10/2010 | Hoff | B21F 45/008 |
| | | | 140/123 |

* cited by examiner

ROBOTICALLY SHAPING A GUIDE WIRE TIP

CROSS-REFERENCE TO RELATED PATENT APPLICATIONS

This application is a continuation of U.S. application Ser. No. 14/216,728, entitled ROBOTICALLY SHAPING A GUIDE WIRE TIP filed Mar. 17, 2014, which claims the benefit of U.S. Provisional Application No. 61/790,272 entitled ROBOTICALLY SHAPING A GUIDE WIRE TIP filed Mar. 15, 2013 both of which are incorporated herein by reference in their entirety.

BACKGROUND

Guide wires are used to facilitate percutaneous procedures in which the guide wire is threaded into a human patient using X-ray guidance. The guide wires are manually threaded by a physician or other medical personnel but this requires that the operator be adjacent to the patient and so be in the immediate vicinity of the X-ray radiation providing the image used for guidance. Systems have been developed, such as that disclosed in U.S. Pat. No. 7,887,549 incorporated herein by reference, which allow the guide wires to be threaded into the patient robotically and thus allow the user or operator to be remote from the patient and the X-ray radiation. The tip of the guide wire may be manually shaped into an arcuate shape to assist in the navigation of the guide wire.

SUMMARY

In one embodiment a robotic system for driving a guide wire into a human patient includes a robotic tool to change shape the tip of the guide wire and a robotic control system providing signals to operate the guide wire shaping tool.

Another embodiment includes a process for changing the shape of a tip of a guide wire with a robotic drive including feeding a portion of a guide wire into a tip shaping mechanism. The process also includes robotically operating the tip shaping mechanism to cause the tip of the guide wire to be plastically deformed such that it is directed away from a longitudinal axis of the guide wire. The process further includes robotically feeding the guide wire with the shaped tip into a vessel in a human patient.

In another embodiment, a system for providing a robotically driven guide wire with a shaped tip to a guide catheter includes a tip shaping mechanism which causes the tip of the guide wire to be plastically deformed such that it is directed away from the axis of the guide wire. A robotic drive mechanism feeds the guide wire to the tip shaping mechanism.

DETAILED DESCRIPTION

Figure 1:
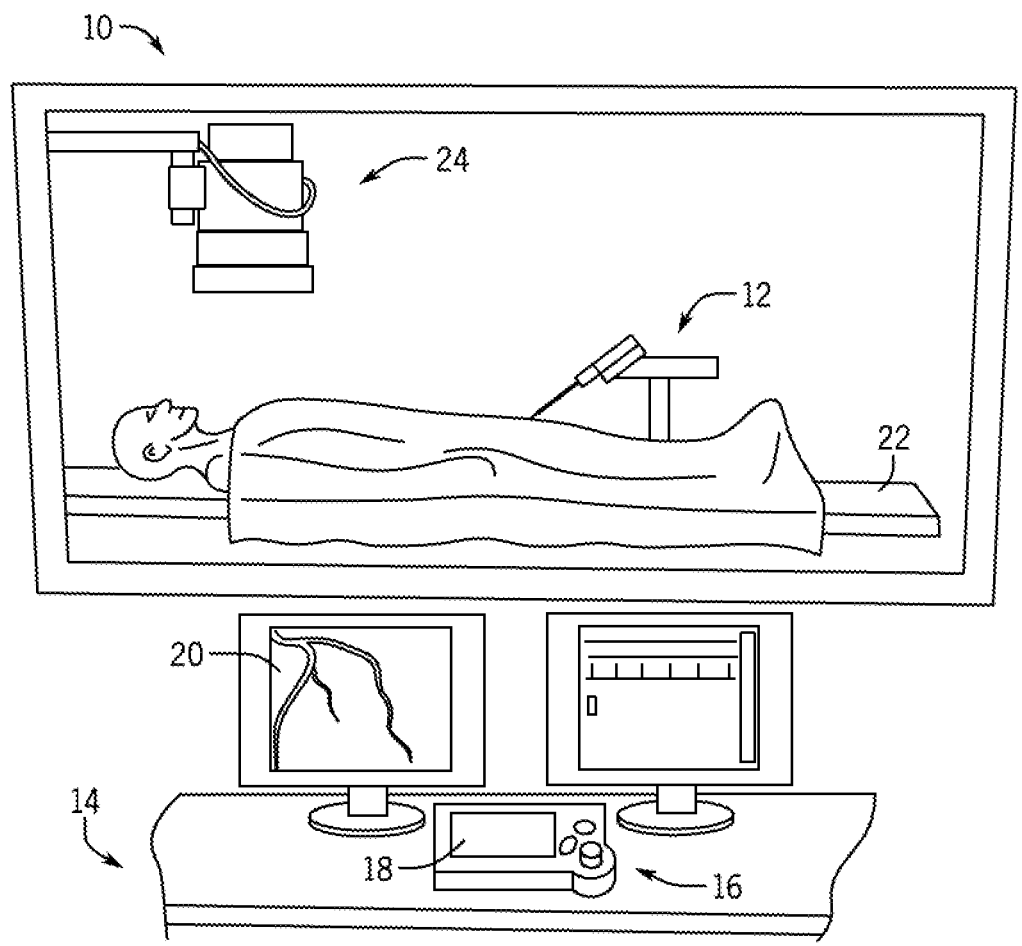
FIG. 1 is a schematic view of a robotic system for remotely moving a guide wire in a patient.

Referring to FIG. 1 a robotic system for manipulating an elongated medical device includes a bed side station 12 proximate a bed 22. A remote control station 14 includes a controller 16 having a user input 18 to control the bed side station 12. An x-ray source 24 is used in a Fluoroscopy system to provide an image on a display 20 in remote station 14. A robotic system such as that described in U.S. Pat. No. 7,887,549 may be used in conjunction with the wiper mechanism described herein.

Figure 2:
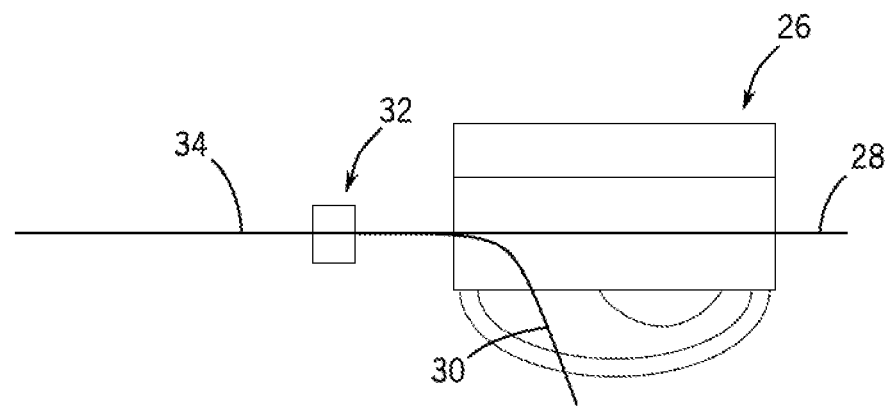
FIG. 2 to a schematic top plan view of a robotic drive and a wire shaping tool.

Referring to FIG. 2, in one embodiment a robotic shaping tool device 32 is positioned intermediate guide catheter 34 and the guide wire drive mechanism in cassette 26. It is also contemplated to position robotic shaping tool device 32 separate from cassette 26 or on a distal end portion of cassette 26. By positioning robotic shaping tool device 32 on the distal end or distal portion of cassette 26 it is possible to provide a shape to the guide wire tip without removing the guide wire from the drive mechanisms within cassette 26. In another embodiment, robotic shaping tool device 32 may be positioned on a proximal end of cassette 26. It is contemplated that a portion of the guide wire 28 may be positioned within the drive mechanism or mechanisms within cassette 26 and a sufficient length of the guide wire 28 may extend from the distal end of the cassette so that the tip may be shaped in a robotic shaping tool device 32 positioned above, below, to the right or left of cassette 26. In one embodiment a proposed tip shape could be tested using simulation software. A proposed tip shape could be run through a simulation and the results used to adjust how the shaping tools are instructed. In one embodiment, a working elongated medical device such as a balloon stent catheter 30 is driven longitudinally by a drive mechanism within cassette 26 and the robotic shaping tool device 32 is located between the drive mechanism for the working catheter and the guide catheter 32.

Figure 3:
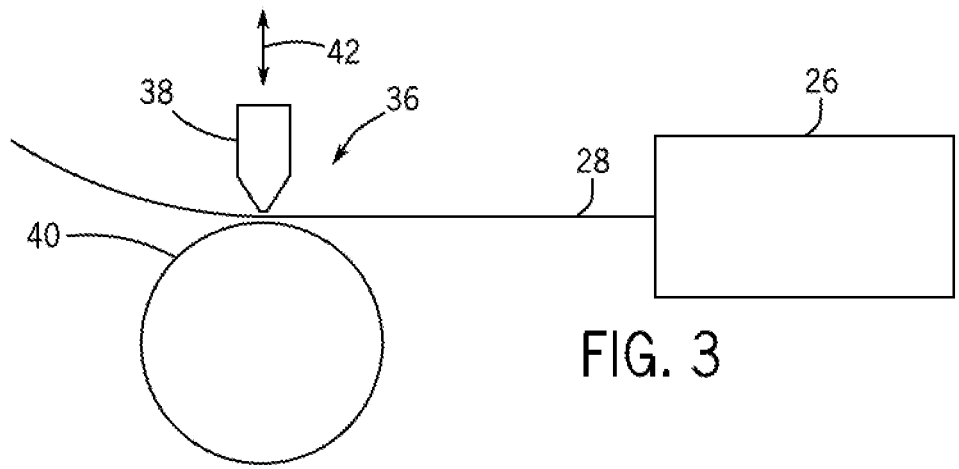
FIG. 3 is a schematic view of a first robotic wire shaping tool.

Referring to FIG. 3, robotic drive mechanism 26 feeds guide wire 28 to an anvil based tip shaping mechanism 36. Anvil based shaping mechanism 36 comprises an anvil 38 with angled faces and a cooperating wheel 40. An application force 42 can be applied to the anvil 38 at various angles to influence the shape imparted to the tip of the guide wire 28.

Figure 4:
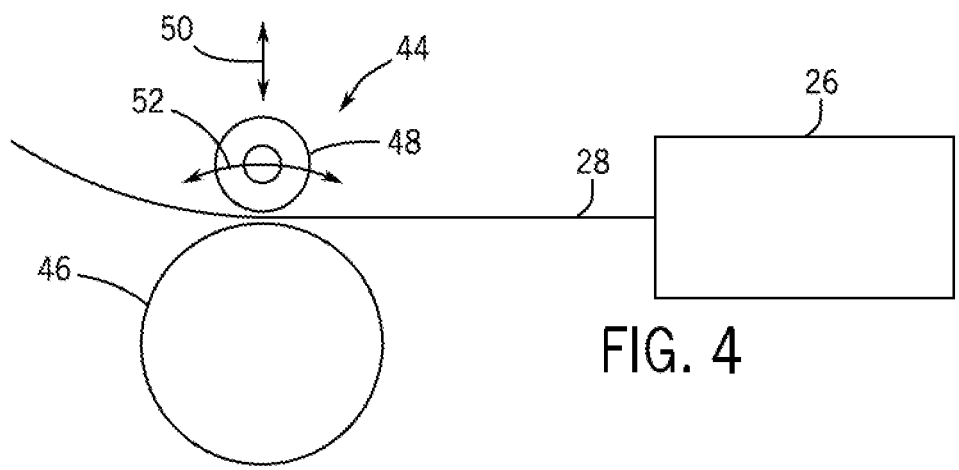
FIG. 4 is a schematic view of a second robotic wire shaping tool.

Referring to FIG. 4, robotic drive mechanism 26 feeds guide wire 28 to a roller based tip shaping mechanism 44. Roller based tip shaping mechanism 44 comprises a roller 48 and a cooperating wheel 40. Roller 48 has an adjustment path 52 which facilitates addressing guide wire 28 in such a way that the path of guide wire 28 is diverted from a straight line from drive 26 to mechanism 44. Force 50 causes roller 48 to press guide wire 28 against wheel 46.

Figure 5:
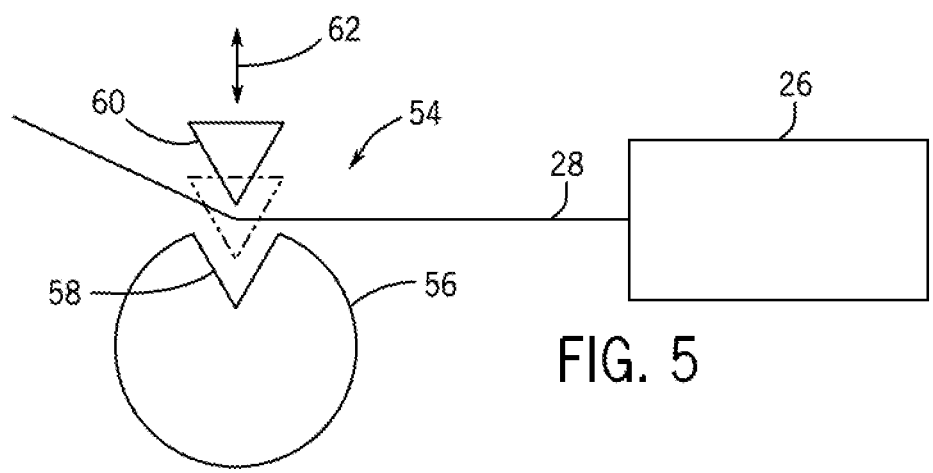
FIG. 5 is a schematic view of a third robotic wire shaping tool.

Referring to FIG. 5, robotic drive mechanism 26 feeds guide wire 28 to a fixed shaping tool based tip shaping mechanism 54. Fixed shaping tool based mechanism 54 comprises a finger 60 which is pressed into a shaped recesses 58 in a fixed shaping tool 56 by a force 62.

Figure 6:
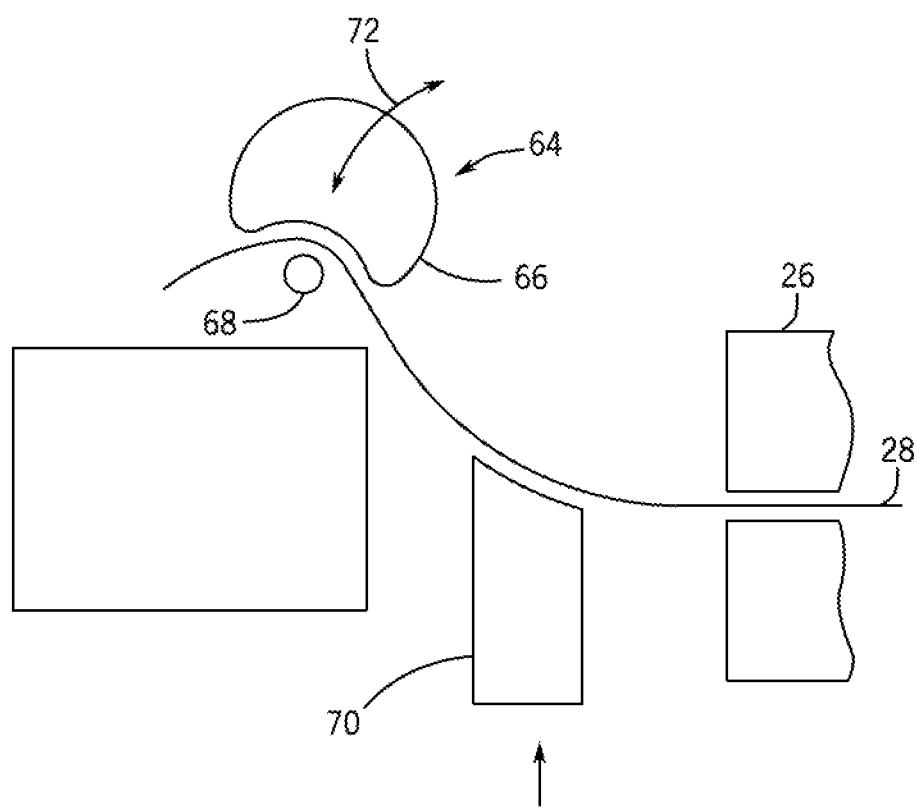
FIG. 6 is a schematic view of a fourth robotic wire shaping tool.

Referring to FIG. 6, robotic drive mechanism 26 feeds guide wire 28 to a variable shaping tool based tip shaping mechanism 64. Variable shaping tool based shaping mechanism 64 comprises a variable shaping tool 66 and a cooperating cylindrical finger 68. Variable shaping tool 66 has a variable surface and force 72 determines what portion of that face interacts with guide wire 28 and cylindrical finger 68.

The portions of shaping tool 66 that contact guide wire 28 may be elastomeric. A diverter 70 directs guide wire 28 along a first path from robotic drive 26 to mechanism 66.

In one embodiment the tip of the guide wire is forced against a post or anvil with an appropriately shaped tool to angle the tip away from the axis of the guide wire. The action is similar to the action of drawing a decorative packaging ribbon over a scissors to impart a curl. In one embodiment the anvil and tool are positioned between the end of the robotic system which delivers the guide wire and the human patient and in another embodiment it is placed earlier in the delivery path. In the former case it may be necessary to withdraw the guide wire, shape its tip and then retract the guide wire while in the latter case it may be possible to shape the tip as the guide wire is being feed through the robotic system. Two approaches to shaping tools positioned in accordance with the former approach are shown in the attached drawing.

In one embodiment the controls for the tools such as the anvil or post and shaping tool may include suggested shaping routines. In one embodiment the system may contain software that examines an X-ray image of the anticipated path of the guide wire and then proposes a particular shaping routine.

In one embodiment the system may provide an image of the shaped tip to the user. This would allow the user to operate the tools to better conform the tip to the desired shape in cases in which the initial routine failed to do. Thus the image could act as a quality control and eliminate the need to leave the control console and physically inspect the shaped tip.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A process for changing a shape of a tip of a guide wire comprising:
   feeding a portion of the guide wire into a tip shaping mechanism having a first member moving relative to a second member;
   a control system providing signals operating the tip shaping mechanism to cause the tip of the guide wire to be plastically deformed such that the tip of the guide wire is directed away from a longitudinal axis of the guide wire.

2. The process of claim 1 wherein the guide wire is fed to the tip shaping mechanism following a first path that is separate from a second path that leads into a guide catheter, then withdrawing the guide wire with the shaped tip and then feeding the guide wire with the shaped tip along the second path into the guide catheter.

3. The process of claim 2 wherein a diverter comprising a surface is used to guide and direct the guide wire into the first path.

4. The process of claim 1 wherein the tip shaping mechanism lies along a path that leads into a guide catheter.

5. The process of claim 1 wherein the tip shaping mechanism is provided along a path that the guide wire is to follow into a vessel in a human patient.

6. The process of claim 1 further comprising providing an image of the shaped tip with an imaging mechanism before the shaped tip is fed to a guide catheter.

7. The process of claim 5 further comprising providing an image of the shaped tip with an imaging mechanism.

8. The process of claim 6 further comprising changing an initial shape of the shaped tip with the tip shaping mechanism based upon the image.

9. The process of claim 1 wherein the control system proposes a particular shaping routine and provides instructions to the tip shaping mechanism.

10. The process of claim 1 wherein the operating of the tip shaping mechanism involves moving the guide wire along the longitudinal axis.

11. The process of claim 10 wherein a speed at which the guide wire is moved past the tip shaping mechanism is used to affect the shape of the tip.

12. The process of claim 10 wherein an angle between the guide wire and first member and the second member of the tip shaping mechanism is used to affect the shape of the tip.

13. The process of claim 10 wherein one of the first member and the second member of the tip shaping mechanism includes a channel to receive the guide wire, wherein a configuration of the channel is changed to affect the shape of the tip and wherein the guide wire is then withdrawn from the tip shaping mechanism.

14. The process of claim 13 wherein one of the first and second members of the tip shaping mechanism that defines the channel includes elastomeric material that interacts with the guide wire.

15. A system for providing a robotically driven guide wire with a shaped tip to a guide catheter comprising:
   a control system providing signals to a tip shaping mechanism having a first member moving relative to a second member causing the shaped tip of the guide wire to be plastically deformed such that the shaped tip is directed away from a longitudinal axis of the guide wire.

16. The system of claim 15 further including a drive mechanism advancing the guide wire along a first path that leads to the tip shaping mechanism and along a second distinct path that leads to the guide catheter and includes a diverter comprising a surface which directs the guide wire into the first path.

17. The system of claim 16 wherein the first member comprises a finger that presses the guide wire into the second member.

18. The system of claim 17 wherein a portion of the second member that interacts with the guide wire is elastomeric.

19. The system of claim 15 further including an imaging mechanism that creates an image of the shaped tip and provides the image to an operator of the system.

* * * * *